US012605378B2

(12) United States Patent
Sensoy et al.

(10) Patent No.: US 12,605,378 B2
(45) Date of Patent: Apr. 21, 2026

(54) SMALL THERAPEUTIC MOLECULES CAPABLE OF INHIBITING THE CATALYTIC ACTIVITY OF THE MAIN PROTEASE ENZYME OF SARS-CoV-2

(71) Applicant: ISTANBUL MEDIPOL UNIVERSITESI, Istanbul (TR)

(72) Inventors: Özge Sensoy, Beykoz (TR); Metehan Ilter, Beykoz (TR); Hanife Pekel, Beykoz (TR)

( * ) Notice: Subject to any disclaimer, the term of this patent is extended or adjusted under 35 U.S.C. 154(b) by 459 days.

(21) Appl. No.: 18/255,396

(22) PCT Filed: Dec. 5, 2021

(86) PCT No.: PCT/TR2021/051353

§ 371 (c)(1),
(2) Date: Jun. 1, 2023

(87) PCT Pub. No.: WO2022/119548

PCT Pub. Date: Jun. 9, 2022

(65) Prior Publication Data

US 2024/0115567 A1 Apr. 11, 2024

(30) Foreign Application Priority Data

Dec. 5, 2020 (TR) ................................ 2020/19788

(51) Int. Cl.

| | |
|---|---|
| ***A61K 31/502*** | (2006.01) |
| ***A61K 31/4196*** | (2006.01) |
| ***A61K 31/517*** | (2006.01) |
| ***A61K 45/06*** | (2006.01) |
| ***A61P 31/14*** | (2006.01) |

(52) U.S. Cl.

CPC ........ *A61K 31/502* (2013.01); *A61K 31/4196* (2013.01); *A61K 31/517* (2013.01); *A61K 45/06* (2013.01); *A61P 31/14* (2018.01)

(58) Field of Classification Search

None

See application file for complete search history.

(56) References Cited

U.S. PATENT DOCUMENTS

2020/0317668 A1 10/2020 Graci et al.

FOREIGN PATENT DOCUMENTS

WO 2020241759 A1 12/2020
WO 2020243457 A1 12/2020

OTHER PUBLICATIONS

CAS 688355-46-6. CAS Registry File Accessed Nov. 3, 2025 from STN, entered into STN Jun. 2, 2004 (Year: 2004).*

CAS 910434-17-2. CAS Registry File Accessed Nov. 3, 2025 from STN, entered into STN Oct. 15, 2006. (Year: 2006).*

CAS 1119238-64-0. CAS Registry File Accessed Nov. 3, 2025 from STN, entered into STN Mar. 11, 2009. (Year: 2009).*

International Search Report for corresponding PCT/TR2021/051353 dated Mar. 1, 2022.

(Continued)

*Primary Examiner* — Jennifer A Berrios
*Assistant Examiner* — Sophia Reilly
(74) *Attorney, Agent, or Firm* — EGBERT, MCDANIEL & SWARTZ, PLLC

(57) ABSTRACT

The present invention relates to molecules represented with Formula (I), Formula (II), and Formula (III) and the use of these molecules in the treatment of SARS-CoV-2.

(I)

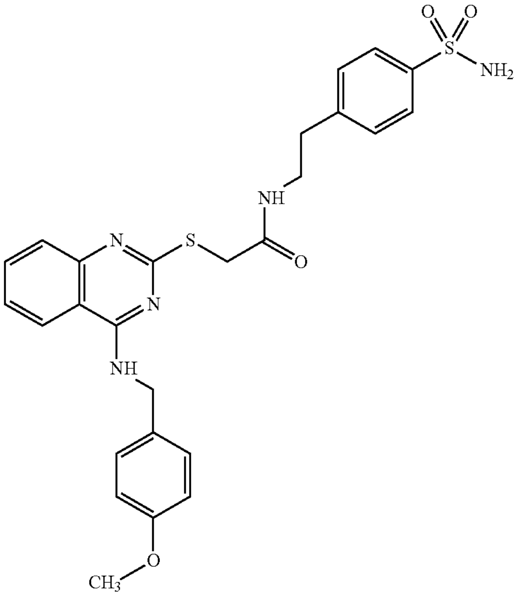

(II)

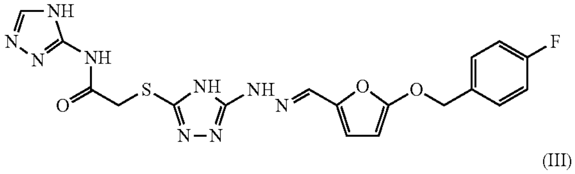

(III)

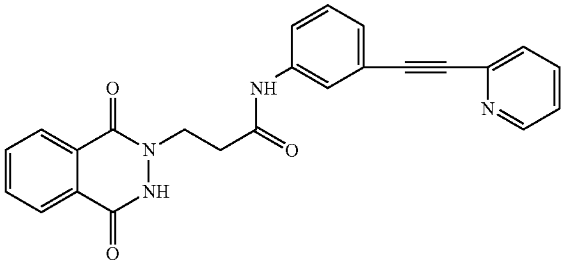

2 Claims, No Drawings

(56) References Cited

OTHER PUBLICATIONS

Written Opinion of the International Searching Authority for corresponding PCT/TR2021/051353 dated Mar. 1, 2022.

* cited by examiner

SMALL THERAPEUTIC MOLECULES CAPABLE OF INHIBITING THE CATALYTIC ACTIVITY OF THE MAIN PROTEASE ENZYME OF SARS-CoV-2

The present invention relates to molecules represented with Formula I, Formula II, and Formula III and to the use of said molecules in the treatment of SARS-CoV-2.

STATE OF THE ART

Having broken out in Wuhan, China in December 2019, Coronavirus disease (COVID-19) spread around the world at an unprecedented pace. COVID-19 is defined as the acute respiratory syndrome stemming from coronavirus-2 (SARS-CoV-2) and transmitting from one individual to another via the respiratory route. As of March 2020, the virus was declared by the World Health Organization to have caused a pandemic. The most common symptoms include dry cough, shortness of breath, nasal congestion, abnormal phlegm production, and fever. The virus additionally leads to organ/system dysfunction, particularly in the late stage. The majority of deaths fundamentally originates from multiple organ failure induced by pneumonia, acute respiratory distress syndrome (ARDS), and excessive increase of inflammatory cytokines.

Comprehensive studies on genomics demonstrated that SARS-CoV-2 possesses approximately 30.000 nucleotides, shares 82% of the sequence identity of SARS-CoV, and therefore, is a member of Beta-coronaviruses. In addition to high similarity in terms of sequence identity, pathogenesis of SARS-CoV-2 bears significant resemblance to SARS-CoV. The pathogenesis of SARS-CoV-2 is characterized by the binding of the spike protein of SARS-CoV-2 to angiotensin converting enzyme-2 (ACE-2) found in lung, nasopharynx, and intestinal epithelium of the host. Subsequent to the cell entry, the viral RNA initiates the translation of polyproteins in ribosome, i.e., polyprotein-1a and polyprotein-1ab. Polyproteins mentioned above are further processed by the main protease (M-pro) and protease similar to papain.

Because of the resemblance of SARS-CoV-2 to SARS-CoV, several drug molecules (hydroxychloroquine, favipiravir, remdesivir, lopinavir-ritonavir), efficacy of which against SARS-CoV has been proven via in vitro experiments thus far, are also being used in the treatment of COVID-19. Despite the fact that the efficacy and reliability of said drugs in other diseases have been proven, studies with respect to COVID-19 are still ongoing. Even though these drugs are being used out of urgent necessity, their effects directly on the targetable proteins of SARS-CoV-2 virus have yet to be proven.

Being the cause of COVID-19 disease, the M-pro enzyme of SARS-CoV-2 virus is the protein that is responsible for the replication of the virus and therefore, often targeted nowadays in the search of novel therapeutic molecules. Despite the fact that there are candidate molecules capable of inhibiting the enzyme activity by binding to the substrate-binding site of the M-pro enzyme of SARS-CoV-2, many of these molecules, in addition to having electrophilic characteristic, inhibit the enzyme by forming a covalent bond with the 145th cysteine amino acid of the enzyme. However, electrophilic molecules, which form a covalent bond with the enzyme in this manner, suffer from reduced reliability in terms of the side effect profile. Such molecules may induce allergies, tissue damage, as well as carcinogenesis. Therefore, there is a need for molecules that are capable of inhibiting the enzyme activity without forming a covalent bond with the M-pro enzyme of SARS-CoV-2.

OBJECTS OF THE INVENTION

The object of the present invention is to prepare novel molecules that are suitable to be used in the treatment of SARS-CoV-2.

Another object of the present invention is to develop novel molecules to be used in the treatment of SARS-CoV-2.

The object of the present invention is to develop molecules that are capable of inhibiting enzyme activity without forming a covalent bond with the M-pro enzyme of SARS-CoV-2.

DETAILED DESCRIPTION OF THE INVENTION

The present invention relates to molecules represented with Formula I, Formula II, and Formula III that are suitable to be used in the treatment of SARS-CoV-2, or to their pharmaceutically acceptable salts, hydrates, solvates, polymorphs, optical isomers, geometric isomers, enantiomers, diastereomers, and mixtures thereof.

Formula

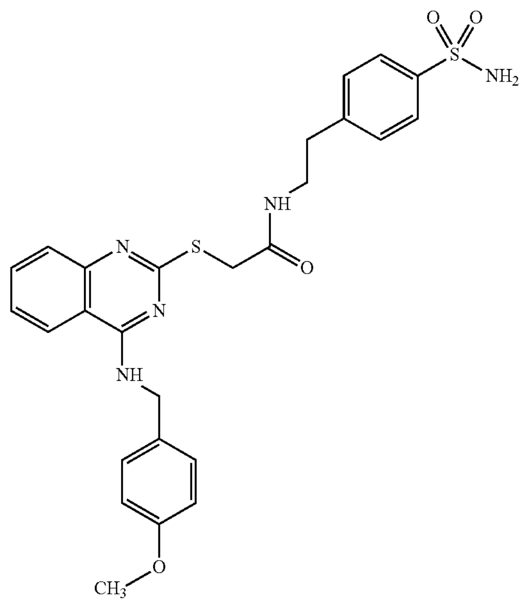

-continued

Formula

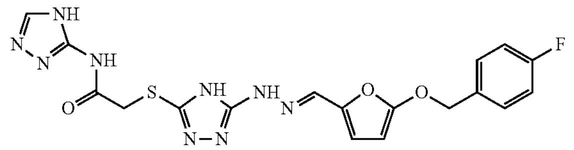

Formula III

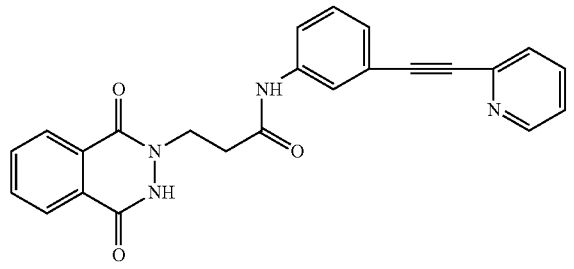

The chemical name of the molecule represented with the aforementioned Formula I is Acetamide, N-[2-[4-(aminosulfonyl)phenyl]ethyl]-2-[[4-[[(4-methoxyphenyl)methyl]amino]-2-quinazolinyl]thio]-. In the detailed description provided herein, this molecule is hereinafter referred to as Formula I or as ZINC2948810, and these names may be used interchangeably.

The chemical name of the molecule represented with the aforementioned Formula II is Acetamide, 2-[[3-[2-[[5-[(4-fluorophenyl)methoxy]-2-furanyl]methylene]hydrazinyl]-1H-1,2,4-triazole-5-yl]thio]-N-1H-1,2,4-triazole-5-yl]-. In the detailed description provided herein, this molecule is hereinafter referred to as Formula II or as ZINC20425029, and these names may be used interchangeably.

The chemical name of the molecule represented with the aforementioned Formula III is 2(1H)-Phthalazinepropanamide, 3,4-dihydro-1,4-dioxo-N-[3-[2-(2-pyridinyl)ethynyl]phenyl]-. In the detailed description provided herein, this molecule is hereinafter referred to as Formula III or as ZINC23881687, and these names may be used interchangeably.

In another aspect, the present invention relates to pharmaceutical compositions comprising molecules represented with Formula I, or Formula II, or Formula III.

In a preferred embodiment of the present invention, said pharmaceutical compositions comprise at least one pharmaceutically acceptable excipient in addition to molecules represented with Formula I, or Formula II, or Formula III.

In a preferred embodiment of the present invention, said pharmaceutical compositions may comprise at least one further active substance in addition to molecules represented with Formula I, or Formula II, or Formula III.

Said further active substance may be any agent known to exhibit activity in the treatment of SARS-CoV-2. Said further active substance, for instance, may be selected from hydroxychloroquine, diosmin, hesperidin, enoxaparin sodium, valsartan, telmisartan, favipiravir, remdesivir, lopinavir, ritonavir, baricitinib, merimepodib, dexamethasone, bamlanivimab, casirivimab and/or imdevimab, amlodipine, losartan, ivermectin, famotidine or dual or triple combinations thereof.

In case at least one further active substance listed above is used in conjunction with compounds of Formula I, Formula II, or Formula III according to the present invention, said further active substance may be administered either concurrently with, or in a sequentially successive manner, or at different times together with agents suitable for Formula I, Formula II, or Formula III.

In another aspect, the present invention relates to Formula I or Formula II or Formula III or to their pharmaceutically acceptable salts, hydrates, solvates, polymorphs, optical isomers, geometric isomers, enantiomers, diastereomers and mixtures thereof for use in the treatment of SARS-CoV-2.

In another aspect, the present invention relates to Formula I or Formula II or Formula III, or to their pharmaceutically acceptable salts, hydrates, solvates, polymorphs, optical isomers, geometric isomers, enantiomers, diastereomers and mixtures thereof for use in the inhibition of SARS-CoV-2 M-pro.

The terms "treatment" or "treating" as used herein refer to inhibiting, relieving, ameliorating, curing, or blocking at least one symptom that characterizes a pathological ailment in a subject who is threatened by an ailment or who suffers from an ailment.

The composition comprising the molecules according to the present invention may in any suitable form based on the preferred method for administering said composition to a patient. The composition comprising the molecules according to the present invention, for instance, may be formulated as liquid dispersions or aqueous or oleaginous suspensions for administration via oral route, or the composition, for instance, may be formulated for parenteral administration including subcutaneous, intravenous, intramuscular, intrasternal, intraperitoneal, intradermal, transdermal administration or similar infusion techniques. The composition comprising the molecules according to the present invention may also be formulated in the form of a spray container for administration via the inhalation route or as a solution for administration through a respiratory equipment or a nebulizer. The molecules according to the present invention are administered to a patient preferably via transdermal, subcutaneous, intranasal, intravenous, intramuscular, intratumoral or respiratory route. In any case, the optimal route for administration may be determined based on the molecules according to the present invention, character and severity of a disease, and physical condition of a patient.

The term comprising within the context of the description provided herein, is intended to imply the meaning of the term includes.

The embodiments of the present invention may be combined where appropriate from a technical aspect.

The embodiments are described herein so as to comprise certain features/components. Moreover, the respective description also comprises other possible embodiments that fundamentally include or consist of said features/components.

Technical references similar to patent documents and application are included in this document by reference.

The embodiments that are specifically and explicitly described herein, be it individually or in combination with one or a plurality of other embodiments, may constitute a basis for a disclaimer.

The present invention will now be described by making references to following examples that are provided only for illustrative purposes and that cannot be construed to impose any limiting effects on the scope of the present invention.

Examples

Diosmin molecule of flavonoid structure, antiviral activity of which is commonly known, is currently on early-stage phase I clinical trial together with hesperidin and low-molecular-weight-heparin for the treatment and prophylaxis of COVID-19. In said clinical trial, hesperidin molecule is being used based on the grounds that it may inhibit cell entry of SARS-CoV-2 virus by affecting the ACE-2 receptor in human cells. However, diosmin molecule is used in combination with hesperidin even though such an activity is mentioned for the diosmin molecule in said clinical trial.

In addition thereto, the results obtained through the simulation of molecular dynamics of α-ketoamide 13b, which is a covalent inhibitor, of which inhibiting activity on the M-pro enzyme of SARS-CoV-2 were proven via in vitro studies, was used as a reference in the development of the present invention.

Accordingly, the diosmin molecule, which is known from the aforementioned clinical trial that it exhibits activity on SARS-CoV-2 based on the results of the ensemble based virtual screening and molecular dynamics conducted for identifying other molecules that bear similar dynamic characteristics to this particular molecule, was observed to change the enzyme dynamics through non-covalent interaction with M-pro enzyme in a way similar to α-ketoamide 13b.

More importantly, molecules of Formula I, Formula II, and Formula III as disclosed in the detailed description provided herein, analogously to the diosmin molecule, demonstrated dynamic changes similar to α-ketoamide 13b on the M-pro enzyme of SARS-CoV-2. This indicates that compounds of Formula I, Formula II, and Formula III according to the present invention exhibits activity on SARS-CoV-2.

In fact, in addition to all of said molecules, eluxadoline, which is a molecule the use of which is approved by the FDA for the treatment of irritable bowel syndrome, also shown dynamics similar to α-ketoamide 13b. Apart from our study, another study conducted without performing simulations on molecular dynamics and by using molecular docking method only predicted that eluxadoline molecule may be effective in the known substrate-binding site of M-pro enzyme. However, no clinical study is available regarding this molecule.

The invention claimed is:

1. A pharmaceutical composition comprising i) at least one compound selected from Formula I, Formula II, Formula III, and salts, hydrates, solvates, polymorphs, optical isomers, geometric isomers, enantiomers, diastereomers thereof for use in the treatment of SARS-COV-2

Formula I

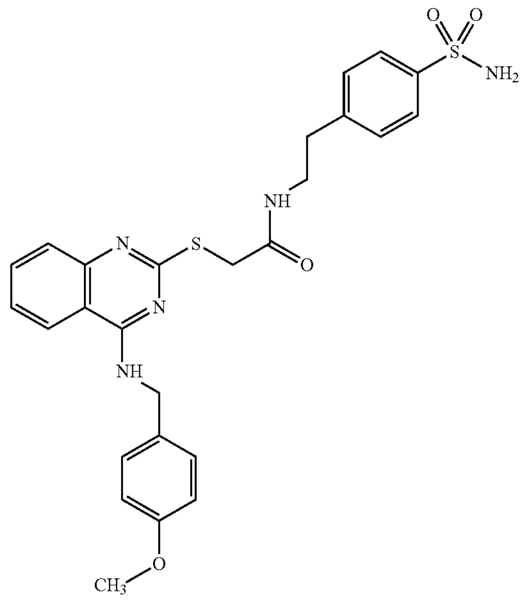

Formula II

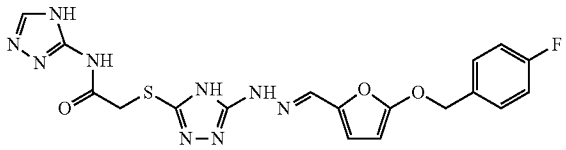

Formula III

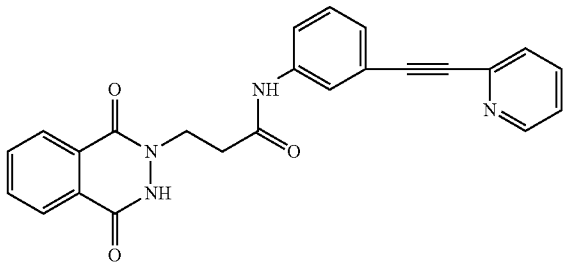

ii) at least one pharmaceutically acceptable excipient.

2. The pharmaceutical composition of claim 1, further comprising:

at least one other active substances selected from hydroxychloroquine, diosmin, hesperidin, enoxaparin sodium, valsartan, telmisartan, favipiravir, remdesivir, lopinavir, ritonavir, baricitinib, merimepodib, dexamethasone, bamlanivimab, casirivimab and/or imdevimab, amlodipine, losartan, ivermectin, famotidine or dual or triple combinations thereof.

* * * * *